(12) United States Patent
Medoff et al.

(10) Patent No.: US 9,220,546 B2
(45) Date of Patent: Dec. 29, 2015

(54) EXPANSION AND COMPRESSION INSTRUMENT FOR FRACTURE FIXATION

(75) Inventors: Robert J. Medoff, Kailua, HI (US); David Anderson, Saugus, CA (US)

(73) Assignee: TRIMED, INC., Valencia, CA (US)

( * ) Notice: Subject to any disclaimer, the term of this patent is extended or adjusted under 35 U.S.C. 154(b) by 1650 days.

(21) Appl. No.: 11/972,935

(22) Filed: Jan. 11, 2008

(65) Prior Publication Data

US 2009/0182345 A1 Jul. 16, 2009

(51) Int. Cl.
- *A61B 17/58* (2006.01)
- *A61B 17/60* (2006.01)
- *A61F 2/00* (2006.01)
- *A61B 17/80* (2006.01)

(52) U.S. Cl.
CPC .................................. *A61B 17/8019* (2013.01)

(58) Field of Classification Search
USPC ...... 606/57, 86 R, 90, 99, 104, 105, 281, 916
See application file for complete search history.

(56) References Cited

U.S. PATENT DOCUMENTS

| | | | |
|---|---|---|---|
| 6,692,503 B2 * | 2/2004 | Foley et al. .................... | 606/96 |
| 2006/0089651 A1 * | 4/2006 | Trudeau et al. ................ | 606/86 |
| 2006/0122597 A1 * | 6/2006 | Jones et al. .................... | 606/61 |
| 2006/0235427 A1 * | 10/2006 | Thomas et al. ............... | 606/105 |
| 2008/0125788 A1 * | 5/2008 | Cohen et al. .................. | 606/104 |

OTHER PUBLICATIONS

A.H. Crenshaw (Editor), Cambell's Operative Orthopaedics, 1992, p. 752-756, vol. 2 eighth ed., Mosby-Year Book Inc., St. Louis, MO USA.

* cited by examiner

*Primary Examiner* — Sameh Boles
(74) *Attorney, Agent, or Firm* — Patzik, Frank & Samotny Ltd.

(57) ABSTRACT

An expansion and compression instrument for fracture fixation. The instrument includes a first handle member, a second handle member, a bearing assembly, and a replaceable tip insert. The bearing assembly axially receives a driver, such as a hexagonal head screwdriver. The replaceable tip insert is adapted to engage an aperture of a fracture fixation plate. The driver is adapted to engage the head of a bone screw, partially threaded into bone proximate the fracture and disposed through a longitudinal slot of the plate. Manual manipulation of the handle members together or apart causes the driver head and replaceable tip insert to become farther apart or closer together, respectively. This in turn, causes the bone screw to be displaced along the longitudinal slot, expanding or compressing the fracture, respectively. Once the fracture has been expanded or compressed to the desired degree, rotation of the screwdriver, facilitated by the bearing assembly, tightens the bone screw, locking the plate into place.

22 Claims, 9 Drawing Sheets

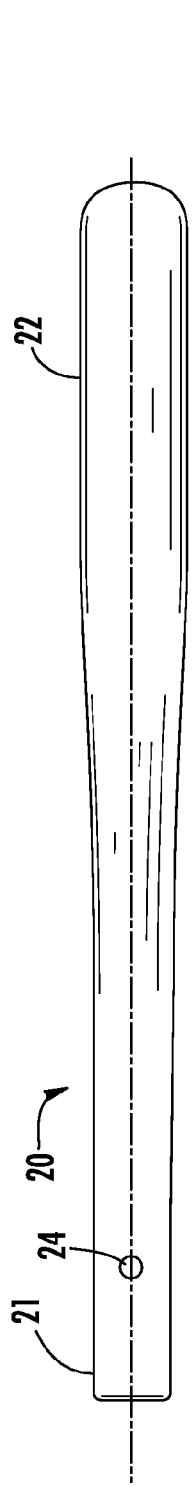
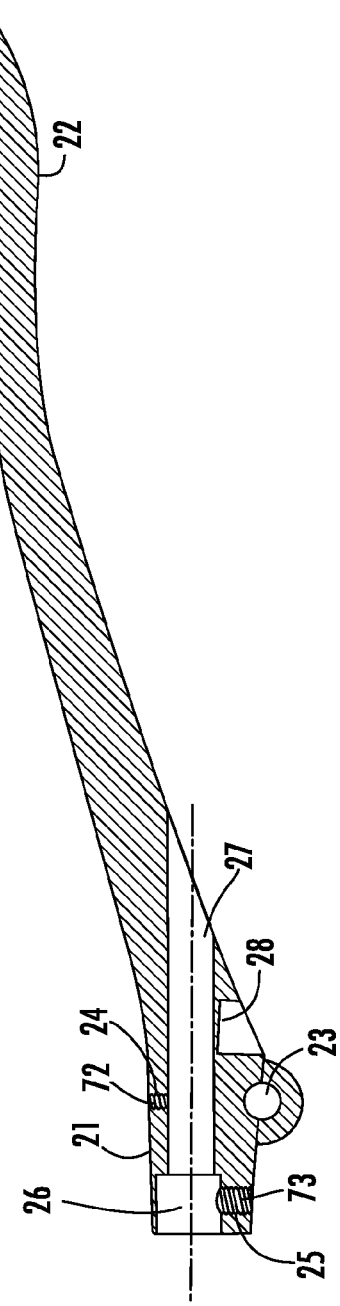
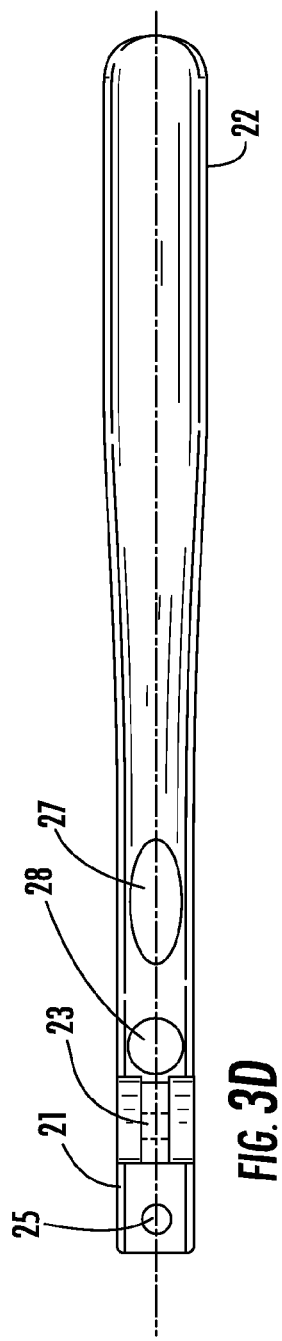
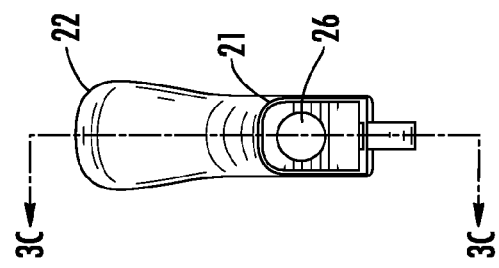
FIG. 3A
FIG. 3C
FIG. 3D
FIG. 3B

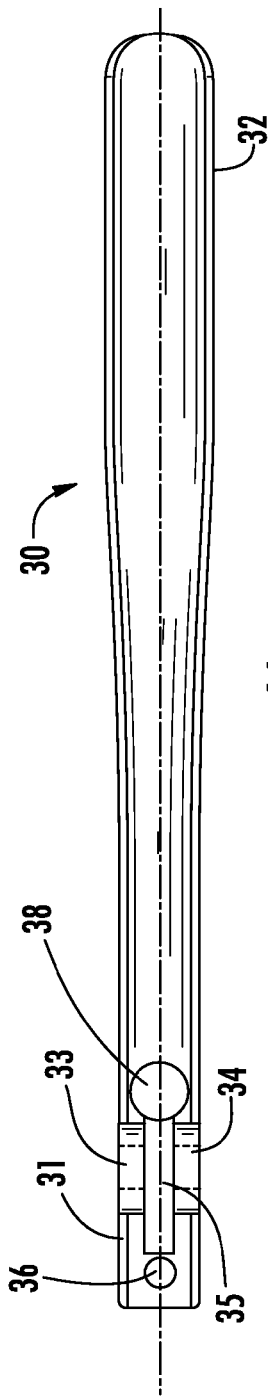
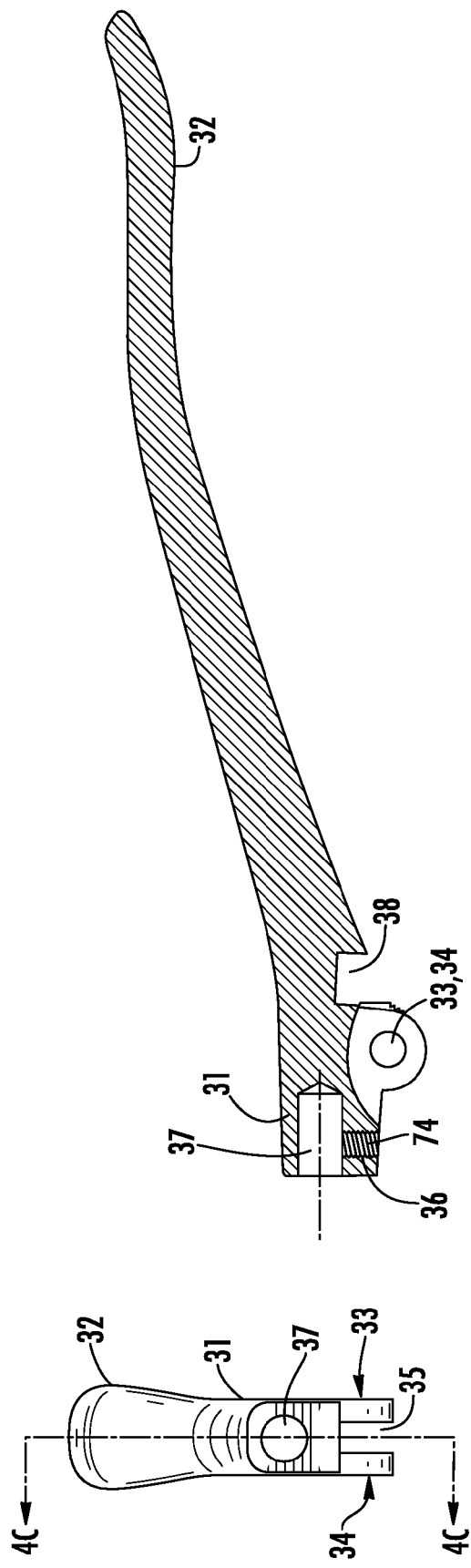
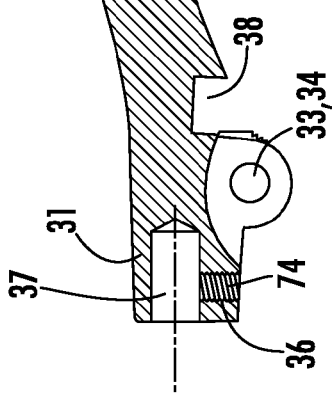
FIG. 4A
FIG. 4C
FIG. 4B

EXPANSION AND COMPRESSION INSTRUMENT FOR FRACTURE FIXATION

BACKGROUND OF THE INVENTION

1. Field of the Invention

The invention relates, in general, to surgical instruments and, more particularly, to surgical instruments for use in the repair of bone fractures.

2. Description of Related Art

In the treatment of certain bone fractures, such as many fractures of the fibula, it is often necessary to distract or separate two bone fragments longitudinally. In such injuries, the two fragments often shorten and override one another. In order to restore alignment, a surgeon must restore length by pulling the fragments apart, back to their normal position. Distraction is also often required for other long bone fractures as well, as the pull of the associated muscles can cause long bone fractures to shorten.

One common method of addressing this shortening of long bone fractures is to manually grasp a distal end of an appendage and manually pull on it longitudinally and away from the proximal end, in order to regain the proper length relationship of the two fragments. However, this can be difficult to perform, as it this requires the surgeon to pull directly against the associated muscles. Moreover, manually pulling on a distal end of a limb does not necessarily produce the required force to distract a fractured bone. In particular, the presence of additional, unfractured bones in the forearm or lower leg will tend to resist any longitudinal pull on the hand or foot, respectively, inhibiting such manual distraction of the fracture. Furthermore, this approach commonly requires two persons to participate: one is required to manually distract the bone fragments, while another applies and tightens the fixation to the fracture.

Another method of distracting is to apply a first bone clamp to a distal portion of the bone above the fracture, apply a second bone clamp to a proximal portion of the bone below the fracture, and then pull the two bone clamps apart. However, a bone clamp may potentially slide on the bone if it is not clamped hard enough. Moreover, if the bone clamp is clamped too hard, it risks crushing or otherwise further damaging the fragment. Also, it is often difficult to generate sufficient clamping force, as the bone clamps are usually not rigidly attached to the respective fragments. Clamping the fragments has two additional disadvantages. Firstly, it requires further soft tissue dissection to expose each bone fragment sufficiently to enable a clamp to be placed around the fragment. Secondly, it may be difficult to apply a plate to the surface of the bone, as the presence of the bone clamps may provide insufficient remaining space in which to position the plate. In other words, a surgeon may use bone clamps to distract the bone fragments to the necessary length, only to discover that a bone plate cannot be readily applied for fixation, as the clamps would first need to be removed, resulting in a loosening of the reduction.

Another method of pulling apart the bone fragments is to first insert a transverse pin into the distal fragment. The distal fragment is then distracted by pulling on the pin. However, this has the undesired effect of creating yet another, temporary hole in the fragment. Moreover, the insertion of any pin can result in inadvertent damage to surrounding nerves or vessels as it is placed across the bone, as it usually requires placement through surrounding soft tissue. Moreover, additional soft tissue exposure can further devascularize the bone and can thus impair healing.

When treating certain bone fractures, situations also arise where it is desirous to create compression, rather than expansion, between two bone fragments adjacent a fracture. For example, a surgeon applying a bone plate may wish to create compression between two bone fragments in order to stimulate healing, as bone fractures typically heal better in compression, in comparison to the absence of compression.

Several techniques have been used for creating compression between bone fragments when a plate is applied. In one technique, a surgeon places a bone screw beyond the end of the plate and applies an outrigger apparatus that couples to the last hole in the plate. Upon turning a screw in the outrigger apparatus, the apparatus pulls the end of the plate towards the screw placed beyond the plate. The surgeon then finishes fixation of the plate, removes the outrigger, and finally removes the outrigger anchoring screw beyond the plate. This technique has the disadvantage of requiring significant additional soft tissue dissection to expose bone proximate the fracture, to enable placement the bone screw and application of the outrigger apparatus beyond the end of the plate. There is also additional required time during surgery to expose the additional bone, to fix the additional bone screw, to apply the outrigger apparatus, and subsequently to remove the outrigger apparatus and additional bone screw.

Another technique for gaining compression is the dynamic compression plate technique. In this technique, a hole in a fixation plate is specially designed to include a countersink portion, to allow a screw head to be seated within the plate, and to further include a squared off profile in cross section at one edge. The head of the bone screw has a rounded cross section. The screw is initially placed up against the end of the hole. As the rounded head of the screw comes down into the hole as the screw is threaded into the underlying bone, it hits the plate, forcing the plate to move sideways to allow the screw head to seat inside the countersink portion of the hole. The dynamic compression plate technique typically requires the fixation plate to have a significant minimum thickness in order to work properly, as the screw head has to sit within the plate. This requirement for a relatively bulky plate can result in irritation of overlying soft tissues, and can result in stress shielding of the bone underneath the relatively thick, stiff plate, potentially resulting in loss of bone mass and osteoporosis. Moreover, the amount of compression displacement achieved from the dynamic compression plate technique is limited by the size of the associated screw head.

BRIEF SUMMARY OF THE INVENTION

In a preferred embodiment, the present invention comprises a surgical tool for performing at least one of relative compression and expansion of a first bone fragment and a second bone fragment in cooperation with a fixation plate, at least one fastener, and a fastener driver having a first end. The surgical tool includes a fixation plate engaging member configured to releasably engage at least a portion of the fixation plate; a driver accepting region permitting at least one of replaceable and permanent attachment of at least a portion of the fastener driver to the surgical tool; and at least one actuator, manipulation of the actuator causing a spacing between the fixation plate engaging member and the first end of the fastener driver to be altered.

The driver accepting region comprises a bore extending through at least a portion of the surgical tool. This bore is sized to permit insertion of at least a portion of the fastener driver therethrough. The fixation plate engaging member comprises a first jaw portion, a second jaw portion, and a plate engaging region disposed between the first and second jaw portions.

In a preferred embodiment, the fixation plate engaging member is releasably attachable to the surgical tool. Alternatively, the fixation plate engaging member may be permanently attached to, or integrally formed with, the surgical tool.

The surgical tool further comprises a bearing assembly adapted to receive at least a portion of the fastener driver. In a preferred embodiment, the bearing assembly is releasably attachable to the surgical tool. Alternatively, the bearing assembly may be permanently attached to, or integrally formed with, the surgical tool.

The at least one actuator preferably includes a gripping region. In a preferred embodiment, the gripping region is a portion of a handle member. The driver accepting region preferably comprises a bore extending through at least a portion of the at least one actuator, and is sized to permit insertion of at least a portion of the fastener driver therethrough.

In a preferred embodiment, the at least one actuator comprises two actuators, including a first handle member and a second handle member. The first handle member has a first gripping region, and the second handle member has a second gripping region. The spacing between the fixation plate engaging member and the first end of the fastener driver increases as the spacing between the first and second gripping regions is decreased. Moreover, the spacing between the fixation plate engaging member and the first end of the fastener driver decreasing as the spacing between the first and second gripping regions is increased. Furthermore, in a preferred embodiment, the two actuators are pivotally attached to each other.

The driver accepting region preferably comprises a bore extending through at least a portion of a first actuator, and the fixation plate fixation member is coupled to at least a portion of a second actuator. The fastener driver may a hexagonal driver, having a hexagonal head. Alternatively, the fastener driver may comprise any of a variety of driver configurations including, but not necessarily limited to, cruciform, Phillips, Torx, or single slotted head screwdriver designs. The fastener driver is preferably releasably attachable to the surgical tool. Alternatively, the fastener driver may be permanently, rotatably attached to at least a portion of the surgical tool. The fastener may comprise a bone screw, such as a self-tapping screw having any of a variety of head configurations, including, but not necessarily limited to, hexagonal, cruciform, Phillips, Torx, or single slotted head screw.

In another embodiment of the present invention, a surgical tool for performing at least one of relative compression and expansion of a first bone fragment and a second bone fragment in cooperation with a fixation plate and at least one fastener is provided, wherein the surgical tool comprises a fixation plate engaging member configured to releasably engage at least a portion of the fixation plate; a driver engaging member permitting releasable engagement of at least a portion of a fastener driver by the surgical tool; and at least one actuator. Manipulation of the actuator causes the spacing between the fixation plate engaging member and the driver engaging member to be altered. In this embodiment, the driver engaging member preferably comprises a first prong member, a second prong member, and a slotted region disposed between the first and second prong members.

In yet another embodiment of the present invention, a surgical tool for performing at least one of relative compression and expansion of a first bone fragment and a second bone fragment in cooperation with a fixation plate and at least one fastener is provided, wherein the surgical tool comprises a fixation plate engaging member configured to releasably engage at least a portion of the fixation plate; a fastener engaging member configured to releasably engage at least a portion of the fastener; and at least one actuator. Manipulation of the actuator causes the spacing between the fixation plate engaging member and the fastener engaging member to be altered. In this embodiment, the fastener engaging member comprises at least one of a U-shaped member and a V-shaped member and is configured to engage a shaft portion of a bone screw underneath a screw head of the bone screw.

BRIEF DESCRIPTION OF THE SEVERAL VIEWS OF THE DRAWINGS

FIG. 3A is a top plan view of the first handle member of the present expansion/compression instrument;

FIG. 3B is an elevated front view of the first handle member of the present expansion/compression instrument;

FIG. 3C is an elevated sectional view of the first handle member of the present expansion/compression instrument, taken generally along lines 3C-3C of FIG. 3B;

FIG. 3D is a bottom view of the first handle member of the present expansion/compression instrument;

FIG. 4A is a bottom view of the second handle member of the present expansion/compression instrument;

FIG. 4B is an elevated front view of the second handle member of the present expansion/compression instrument;

FIG. 4C is an elevated sectional view of the second handle member of the present expansion/compression instrument, taken generally along lines 4C-4C of FIG. 4B;

DETAILED DESCRIPTION OF THE INVENTION

Figure 1:
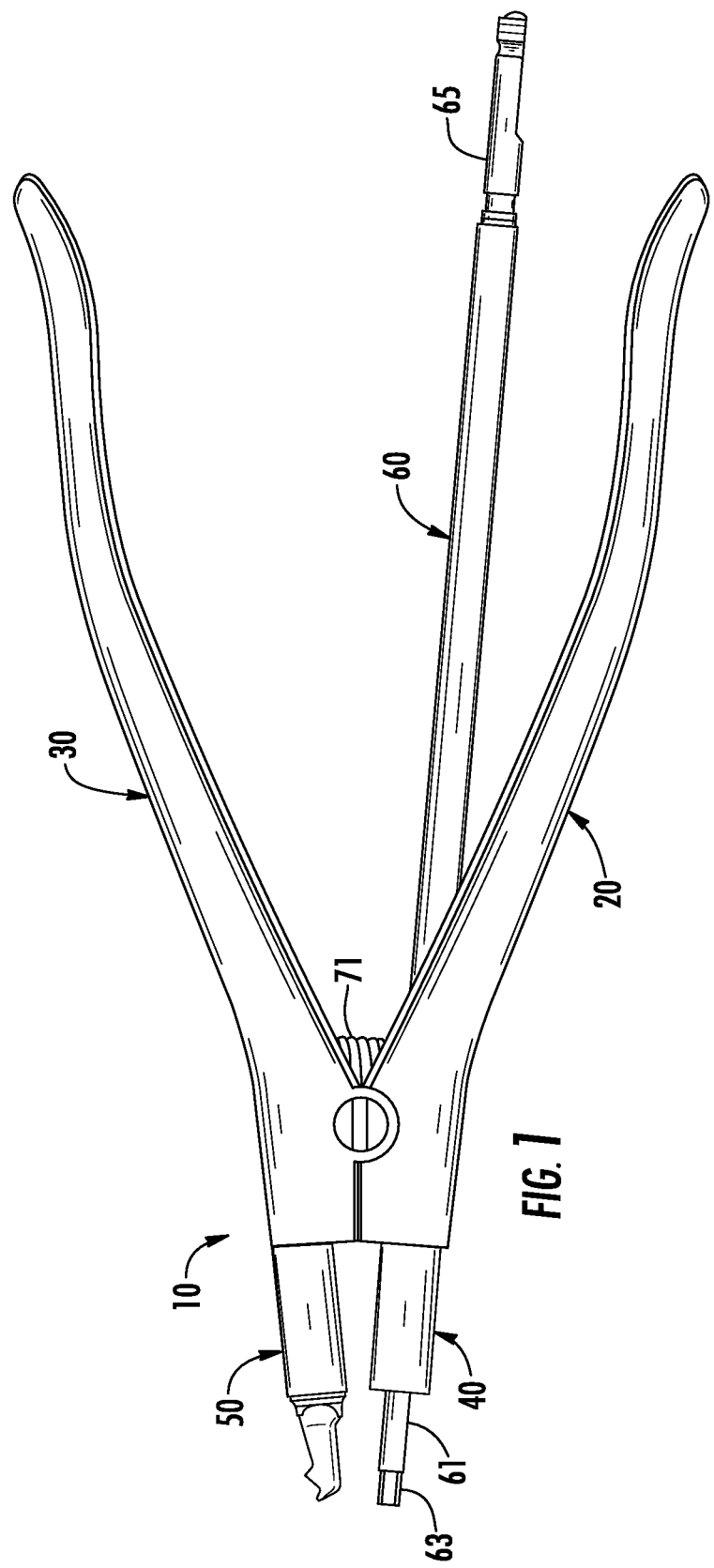
FIG. 1 of the drawings is an elevated side view of a preferred embodiment of the present expansion/compression instrument.

While two different embodiments of the present invention are shown in the various figures, common reference numerals in the figures denote similar or analogous elements or structure amongst the various embodiments.

Figure 2:
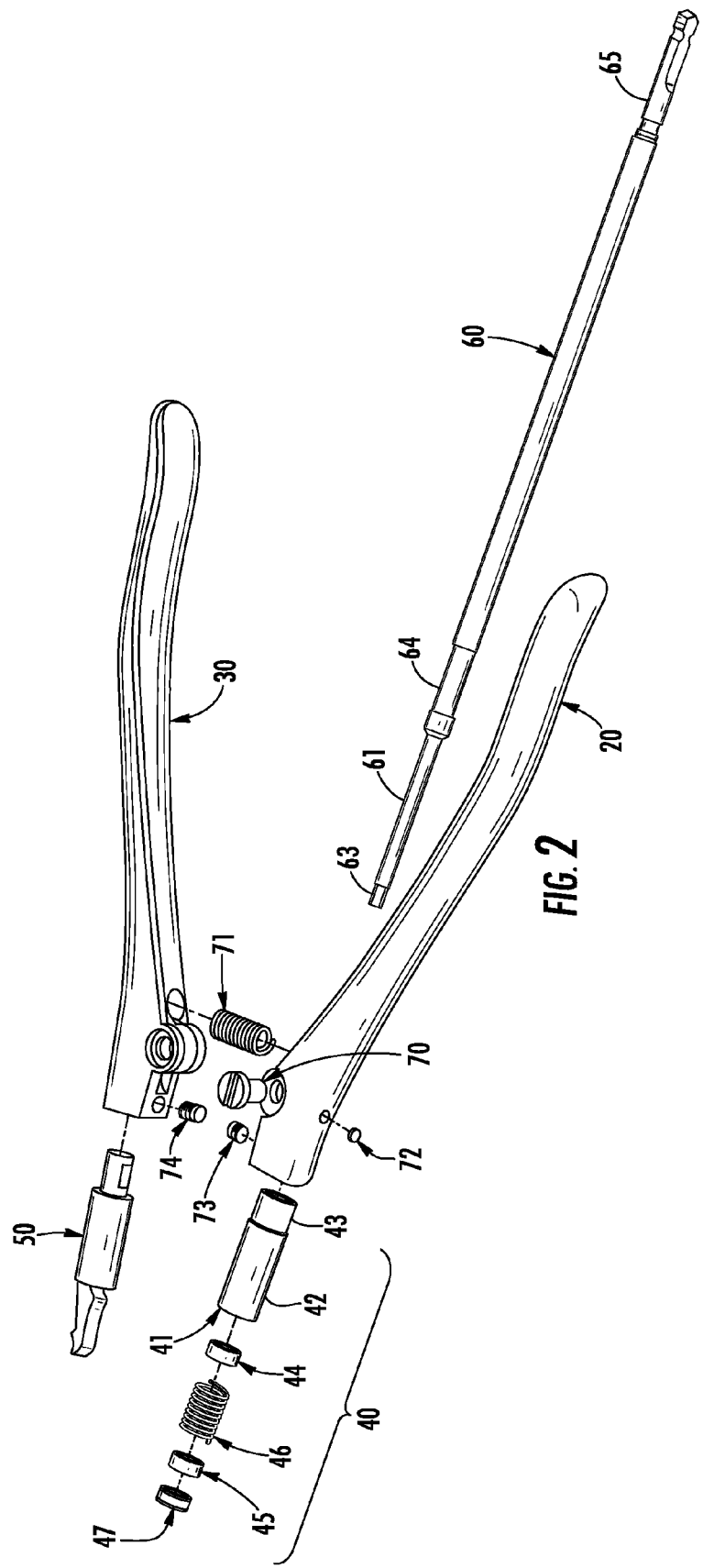
FIG. 2 of the drawings is an elevated exploded perspective view of the present expansion/compression instrument.
Figure 5A:
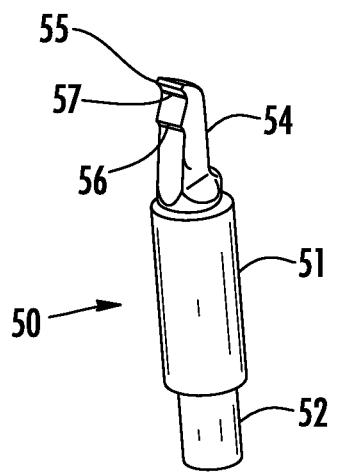
FIG. 5A is an elevated perspective view of the tip insert portion of the present expansion/compression instrument.
Figure 5B:
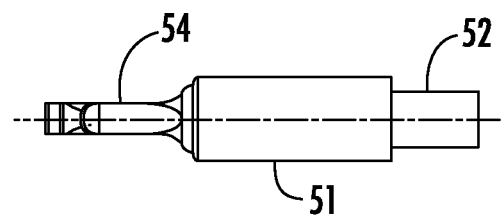
FIG. 5B is a top plan view of the tip insert portion of the present expansion/compression instrument.
Figure 5C:
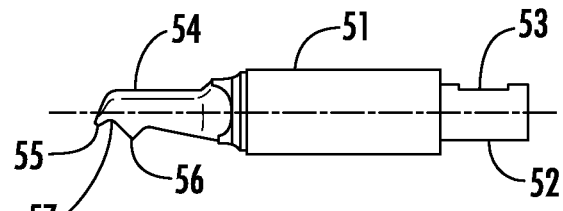
FIG. 5C is an elevated side view of the tip insert portion of the present expansion/compression instrument.
Figure 5D:
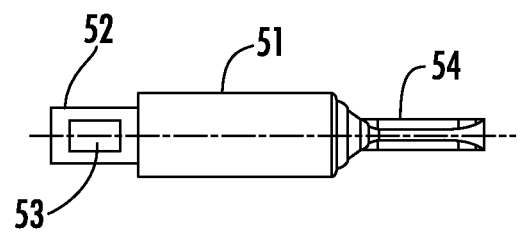
FIG. 5D is a bottom view of the tip insert portion of the present expansion/compression instrument.
Figure 6A:
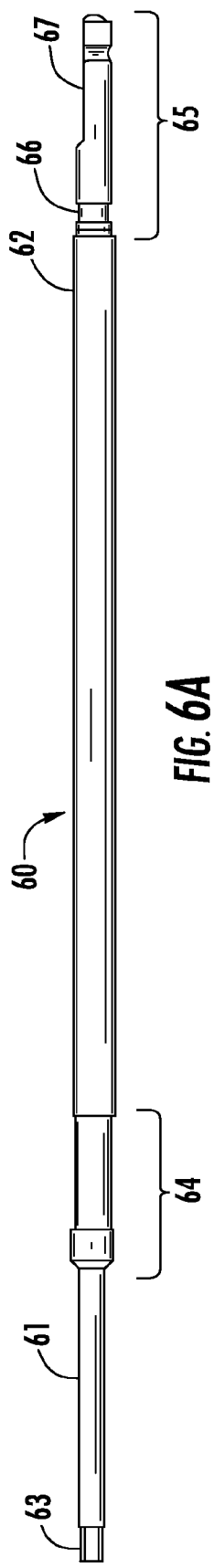
FIG. 6A is an elevated side view of the hex driver portion of the present expansion/compression instrument.
Figure 6D:
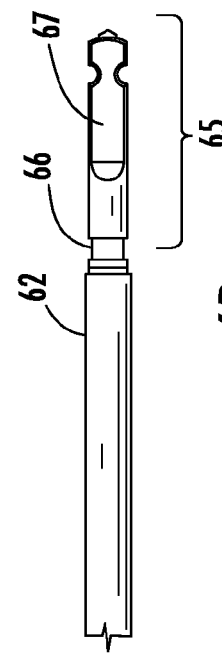
FIG. 6D is a fragmentary, top plan view of the handle attachment region of the hex driver portion of the present expansion/compression instrument.
Figure 6C:
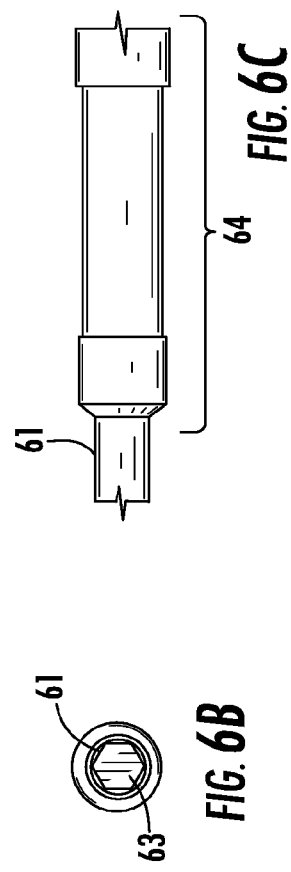
FIG. 6C is an enlarged, fragmentary, elevated side view of the bearing assembly engaging region of the hex driver portion of the present expansion/compression instrument.
Figure 6B:
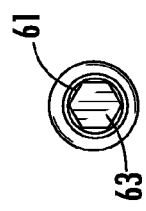
FIG. 6B is an enlarged, elevated front view of the hex driver portion of the present expansion/compression instrument.

A preferred embodiment of the present fracture fixation expansion/compression instrument or surgical tool 10 is shown in FIGS. 1-2 as comprising first handle member 20, second handle member 30, bearing assembly 40, replaceable tip insert 50, and replaceable hexagonal driver 60. Pivot screw 70 pivotably attached first handle member 20 and second handle member 30 together, and handle spring 71 cooperates with associated retention bores in both handle members to resiliently bias second portions of the handle members away from each other and, in turn, to resiliently bias first portions of the handle members, as well as tip insert 50 and a hexagonal tip of driver 60, towards each other.

As shown in FIGS. 1-2, replaceable tip insert 50, which serves as a fixation plate engaging member configured to releasably engage at least a portion of a fixation plate, is releasably received by a cooperating bore disposed within second handle member 30, and is retained in place by tip insert setscrew 74. Bearing assembly 40 is likewise releasably received by a cooperating bore disposed within first handle member 20, and is retained in place by bearing assembly setscrew 73.

Replaceable hexagonal driver 60 is releasably received by a bore forming a driver accepting region permitting attachment of at least a portion of the driver to the surgical tool and disposed within first handle member 20, with first end 61 of the hexagonal driver extending through this bore, and through bearing assembly 40, such that bearing assembly engaging region 64 of driver 60 is disposed within tubular bearing housing 41 of bearing assembly 40. Driver setscrew 72 releasably retains replaceable hexagonal driver 60 in its fully inserted position, yet is preferably not tightened sufficiently to prohibit axial rotation of the hexagonal driver 60.

As shown in FIG. 2, bearing assembly 40 includes substantially tubular bearing housing 41, having first end 42 and second end 43. First end 42 is slightly larger in outer diameter than second end 43, permitting second end 43 to be inserted into a bearing housing accepting bore disposed in first handle member 20, until the larger diameter first end 42 abuts the front outer surface of first handle member 20. Bearing housing 41 is preferably constructed of a surgical stainless steel material, such as type 17-4 precipitation hardened surgical stainless steel, condition H-900.

Bearing assembly 40 further comprises second roller bearing 44, first roller bearing 45, and spring 46, disposed between roller bearings 44 and 45, all carried within the interior of bearing housing 41. Annular press plug 47 is press fit flush against a first aperture of bearing housing 41, securing roller bearing 44, roller bearing 45, and spring 46 within bearing housing 41. Bearing assembly 40, and in particular roller bearings 44 and 45, permits a hexagonal or other type of driver inserted therethrough to freely rotate, even when transverse pressure is placed upon a first portion of the longitudinal length of the driver when expanding or compressing a fracture using the present surgical tool.

First handle member 20 is shown in FIGS. 3A-3D as comprising first end 21, elongated second end 22 forming a first gripping region or first actuator, an arcuate region or lug having first pivot aperture 23 disposed therethrough, driver setscrew aperture 24 threadably receiving driver setscrew 72, bearing assembly setscrew aperture 25 threadably receiving bearing assembly setscrew 73, bearing housing accepting bore 26, driver accepting bore 27, and handle spring accepting bore 28. As shown in FIG. 3C, bearing housing accepting bore 26 and driver accepting bore 27 are in open communication, with bearing housing accepting bore 26 being slightly larger in diameter than driver accepting bore 27. The juncture of smaller diameter driver accepting bore 27 and bearing housing accepting bore 26 accordingly serves as a stop member, limiting further axial insertion of bearing housing 40 within first handle member 20. First handle member 20 is preferably constructed of a surgical stainless steel material, such as type 420 surgical stainless steel.

Second handle member 30 is shown in FIGS. 4A-4C as comprising first end 31, elongated second end 32 forming a second gripping region or second actuator, and two arcuate regions or lugs, each having an associated coaxial aperture 33, 34, with a spacing 35 therebetween sized to permit the insertion of the arcuate region and aperture or lug 23 of first handle member 20, secured for pivotable relative movement by pivot screw 70. Second handle member 30 further comprises tip insert setscrew aperture 36, threadably receiving tip insert setscrew 74, tip insert accepting bore 37, and handle spring accepting bore 38. Second handle member 30 is preferably constructed of a surgical stainless steel material, such as type 420 surgical stainless steel.

Replaceable tip insert 50 is shown in FIGS. 5A-5D as comprising cylindrical body 51, second shaft 52 having flattened, planar region 53, and first tip region 54. First tip region 54 includes first jaw portion 55, second jaw portion 56, and plate engaging region 57, disposed at the junction of jaw portions 55 and 56. Flattened, planar region 53 facilitates the securement of tip insert 50 within tip insert accepting bore 37 of second handle member 30, providing a substantially flat surface for engagement with tip insert setscrew 74, permitting first and second jaw portions 55 and 56 to be secured in an outwardly-facing orientation, away from bearing assembly 40 and first end 61 of hexagonal driver 60, and inhibited from axial rotation away from this orientation.

As cylindrical body 51 is larger in diameter than second shaft 52, the juncture of cylindrical body 51 and second shaft 52 serves as a stop member as second shaft 52 is inserted into a front surface of second handle member 30, inhibiting further axial insertion. Replaceable tip insert 50 is preferably constructed of a surgical stainless steel material, such as 17-4 precipitation hardened stainless steel, condition H-900.

Replaceable tip insert 50 may alternatively have any configuration capable of securely engaging a portion of a fracture fixation plate, and may alternatively comprise, for example, a cylindrical or L-shaped member. Alternatively, the first and second jaw portions 55 and 56 may extend on either side of jaw 54 or completely encircle jaw 54. Moreover, although, in a preferred embodiment, tip insert 50 is removable and replaceable, tip insert 50 may alternatively be permanently attached to, or integrally formed with, second handle member 30.

It may be desirous to use the present invention as a compression instrument, in addition to an expansion instrument. When the present invention is to be used as a compression instrument, it is desirous to have first and second jaw portions of replaceable tip insert 50 disposed in an inwardly facing, rather than an outwardly facing orientation. Accordingly, a second flattened planar region may be disposed on an outer surface of second shaft 52, 180° opposite flattened planar region 53, permitting jaw portions 55 and 56 to be secured in one of two opposing orientations, depending upon whether expansion or compression is to be performed. Alternatively, dedicated replaceable tip inserts may be manufactured and used for the expansion and compression functions of the present invention. A dedicated replaceable tip insert for compression purposes will have a substantially similar design to the expansion tip depicted in FIGS. 5A-5D, with the exception that flattened planar region 53 is disposed on second shaft 52 so as to be on the same side of the tip insert as jaw portions 55 and 56.

Moreover, it is also contemplated that the configuration of first handle member 20 and second handle member 30, and their pivotal interconnection, be modified such that the apparatus operates in a scissors-like manner. In this configuration, squeezing together the elongated second ends of the first and second handle members will cause the respective first ends of the handle members to be pulled together, rather than drawn apart. This configuration may be preferable for applications where the present invention is intended to be used primarily as a compression tool, rather than an expansion tool.

Replaceable hexagonal driver 60 is shown in FIGS. 6A-6D as comprising reduced diameter first end 61, second end 62, hexagonal tip 63, bearing assembly engaging region 64 and handle attachment region 65. Handle attachment region 65 includes ball detent 66 and planar surface portion 67, permitting the releasable attachment of an associated "quick connect" handle, permitting attachment of a variety of interchangeable drivers to a single handle. Bearing assembly engaging region 64 is shaped and sized to be axially received, and then releasably and rotatably retained, within bearing assembly 40. In a preferred embodiment, hexagonal driver 60 is a 2.5 millimeter driver, having a length of approximately 200 millimeters. As hexagonal driver 60 is fully removable, hexagonal drivers of other tip dimensions may instead be used, to accommodate bone screws having hexagonal heads of differing sizes. Moreover, other types of drivers may alternatively be used, selected to match the requirements of an associated bone screw or other fastener. For example, hexagonal driver 60 may be replaced with a cruciform recess screwdriver of an appropriate size, to accommodate bone screws having cruciate heads. Moreover, a Phillips head, Torx, or single slotted driver may likewise alternatively be used.

Replaceable hexagonal driver 60 is preferably constructed of a stainless steel material, such as 455/465 precipitation hardened stainless steel, condition H-900. Although, in a preferred embodiment, driver 60 is removable and replaceable, relative to the remainder of the surgical tool, a single driver 60 may alternatively be permanently attached to, and rotatably carried by, first handle member 20.

Figure 7:
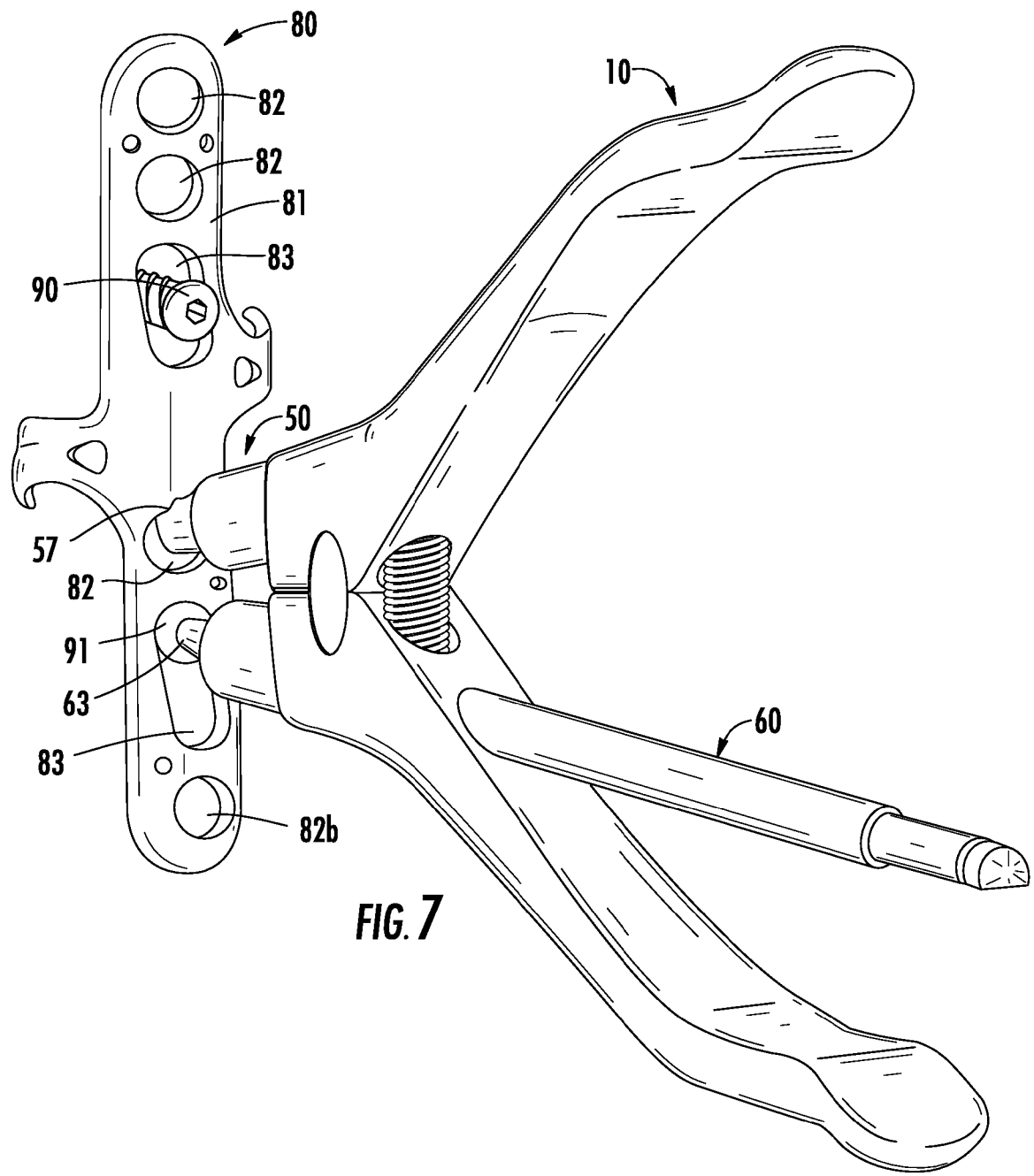
FIG. 7 is an elevated perspective view of the present expansion/compression instrument, showing, in particular, the instrument in use during bone distraction.
Figure 8:
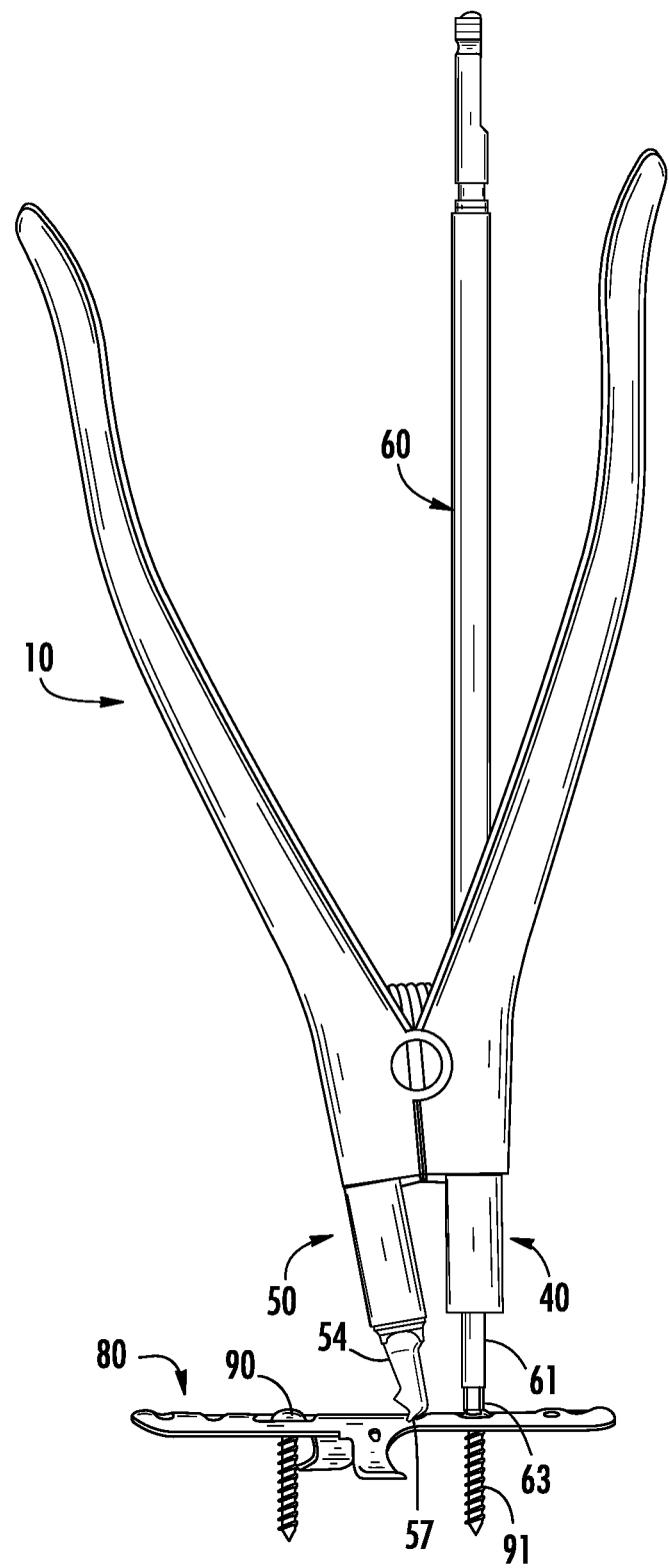
FIG. 8 is an elevated side view of the present expansion/compression instrument, showing, in particular, the instrument in use during bone distraction.

An example of the present fracture fixation expansion/compression instrument 10 in operation while in its expansion configuration is shown in FIGS. 7-8. First, a fracture fixation plate 80, having a body 81, a plurality of annular apertures 82 and a plurality of elongated, slotted apertures 83 is provided. Plate 80 is applied to an incompletely reduced fracture and secured on one side, such as, for example, the distal side of the fracture. In particular, a first bone screw 90 is disposed through an aperture of plate 80 on the distal fragment of the fracture, and is fully secured using an appropriate driver, to fully secure plate 80 to the distal side of the fracture.

Next, a second bone screw 91 is disposed through a slotted aperture 83 of plate 80, overlying the opposite, proximal fragment of the fracture. Second bone screw is partially threaded into the proximal bone fragment, but is not fully tightened against plate 80 at this time.

Fracture fixation expansion/compression instrument 10 is assembled and prepared for use as an expansion tool, preferably prior to the commencement of any surgical procedure, by selecting a replaceable driver 60 of appropriate size and type, relative to the head size and type of the selected associated bone screw, and attaching a suitable handle to the driver. The first end 61 of the appropriate driver is then axially inserted through driver accepting bore 27 and bearing assembly 40 of first handle member 20. The driver is then rotatably locked in its axially inserted position using driver setscrew 72. An appropriate replaceable tip insert 50 is likewise selected, and its second shaft 52 is inserted into tip insert accepting bore 37 of second handle member 30 such that jaws 55 and 56 are placed in an outward facing orientation. Tip insert setscrew 74 is then tightened to releasably lock replaceable tip insert 50 in position.

Next, as shown in FIGS. 7-8, the previously assembled fracture fixation expansion/compression instrument 10 is maneuvered into engagement with plate 80 and second bone screw 91, such that hexagonal tip 63 engages the recessed hexagonal head of bone screw 91, and first jaw portion 55 is at least partially disposed through an aperture 82, such that plate engaging region 57 abuts an edge of aperture 82, as aperture 82 is releasably gripped between jaw portions 55 and 56.

Next, the surgeon applies inward pressure to the two actuators comprising elongated second ends 22 and 32 of first handle member 20 and second handle member 30, respectively, overcoming the spring biasing tension of driver handle spring 71. This, in turn, causes hexagonal tip 63 and replaceable tip insert 50 to become further spaced apart from each other. As plate 80 has been securely affixed to the distal bone fragment using first bone screw 90, this, in turn, cases second bone screw 91 to be displaced away from first bone screw 90, sliding along its associated slotted aperture 83. As second bone screw 91 has been partially threaded into the proximal bone fragment, this, in turn, causes the proximal bone fragment to be displaced away from the distal bone fragment of the fracture. Once a desired spacing of the distal and proximal bone fragments is achieved, through sufficient squeezing together of the gripping regions of the first and second handle members, a handle attached to hexagonal driver 60 is rotated, to fully tighten second bone screw 90 against plate 80, fixing the reduction as desired.

Alternatively, this particular embodiment of the instrument can be simply used as a compression instrument by initial placement of fixation screw 91 at a more peripheral position in the slotted hole and engaging hole 82b at the end of the plate with the gripping jaw. In this application, manual pressure on the second ends 22, 32 of actuators 20, 30 causes hole 82b to displace away from screw 91 and results in compression of a fracture the fracture under plate 80.

As can be seen, as compared to certain prior art methods of distraction discussed above, no additional, temporary holes are required to be placed into the fractured bone. No significant additional soft tissue dissection is required to expose additional surrounding bone, as with an outrigger apparatus or bone clamps. The expansion or compression and fixation tasks can be readily accomplished by a single surgeon, without the requirement of one person to perform the expansion or compression, while another person applies the fixation hardware to the fracture. Moreover, as no clamps are used, any risk of crushing a fractured fragment with the jaw of a clamp is eliminated. Furthermore, as bone screws are rigidly affixed to each bone fragment of the fracture, distraction occurs through rigid points of contact. In addition, as compared to certain prior art methods of distraction, the present invention is more efficient, and provides ease of use, from the surgeon's perspective. Moreover, the present invention permits a single tool, in conjunction with a variety of hexagonal or other drivers and suitable cooperating fracture fixation plates, to be commercially marketed as an overall bone implant system. Finally, in contrast to the dynamic compression plate technique, a relatively thin plate can be used, and the degree of distraction is not limited by the size of the screw head.

Figure 9:
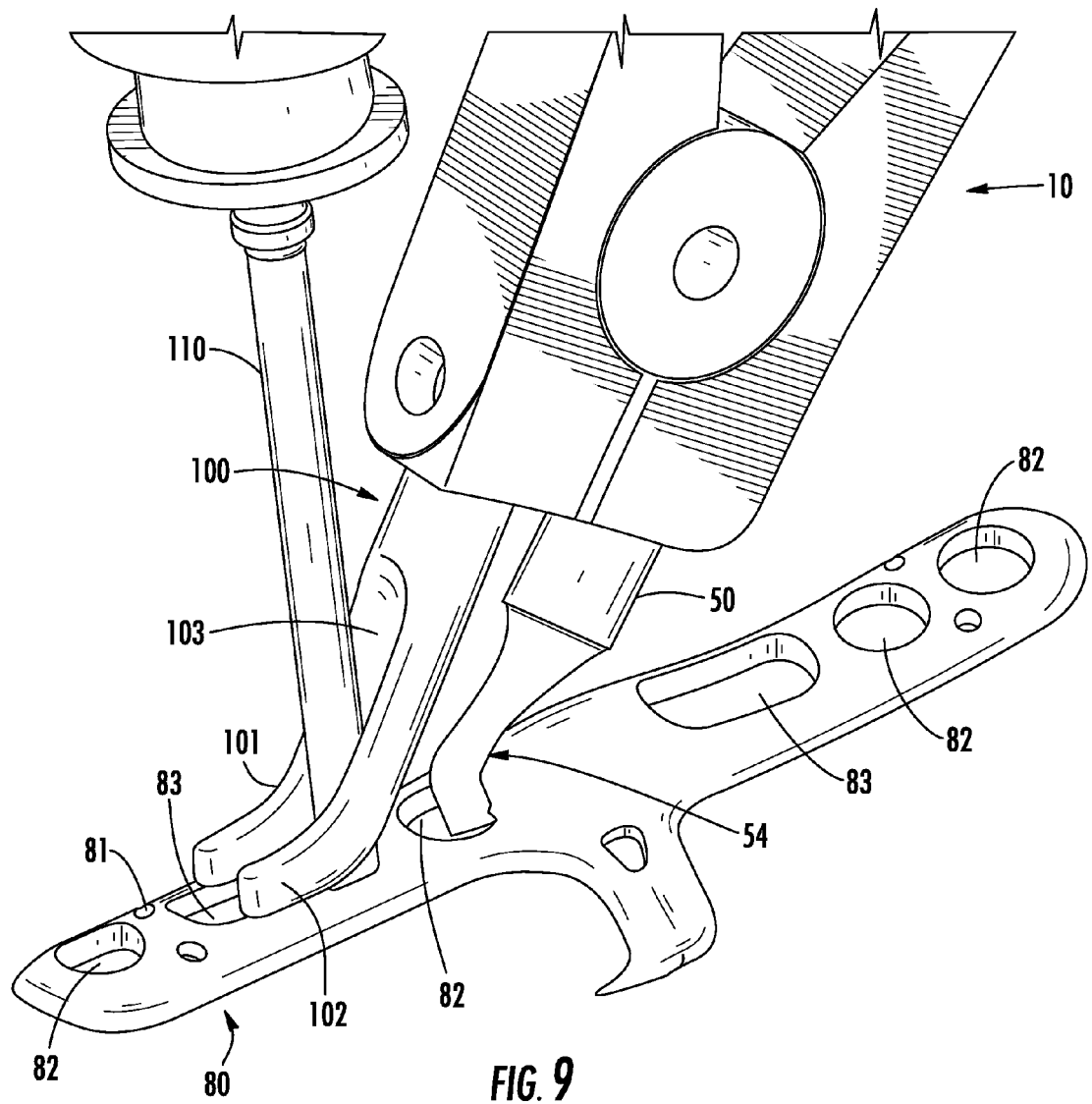
FIG. 9 is an elevated perspective view of another embodiment of the present expansion/compression instrument, showing, in particular, the instrument in use during bone distraction.

An alternative embodiment of the present invention is shown in operation in FIG. 9. In this embodiment, a replaceable tip insert 50, substantially identical to that of the above-described, preferred embodiment, is again employed. However, the bearing assembly and hex driver are instead replaced with a first modified tip insert 100, serving as a driver engaging member and permitting releasable engagement of at least a portion of a fastener driver by the surgical tool. As shown in FIG. 9, modified tip insert 100 comprises first curved prong member 101, second curved prong member 102, and slotted region 103 disposed between the first and second prong members. A conventional driver, such as screwdriver 110, engages the second bone screw that is partially threaded into the proximal bone fragment, but is not fully tightened against plate 80. The shaft of screwdriver 110 is positioned within slotted region 103 of modified tip insert 100. As the handle members of expansion/compression instrument 10 are squeezed together, modified tip insert 100 urges screwdriver 110 and, in turn, the proximal bone fragment, away from replaceable tip insert 50 and away from the distal bone fragment. Once a desired spacing of the distal and proximal bone fragments is achieved, through sufficient squeezing together of the first and second handle members, screwdriver 110 is rotated, to fully tighten the second bone screw against plate 80, fixing the reduction as desired.

A second alternative embodiment substitutes a second modified tip insert for the modified tip insert 100 of FIG. 9. In this embodiment, the second modified tip insert serves as a fastener engaging member and preferably has a curved, generally cylindrical or rod-like shape. One end of the second modified tip insert releasably attaches to first handle member 10, being insertable into a corresponding bore and secured with an associated setscrew. An opposing end of the second modified tip insert terminates in two small prongs, forming an overall U-shape or, alternatively, an overall V-shape. These prongs are sized and configured to be cupped, or wedged underneath the head portion of a bone screw, giving the second modified tip insert the general form of a conventional small pry bar.

In operation, the prongs of this second alternative embodiment may be inserted underneath a partially tightened bone screw. As the handle members of expansion/compression instrument are squeezed together, the second modified tip insert urges the partially tightened bone screw and, in turn, the proximal bone fragment, away from the replaceable tip insert associated with the second handle member, and therefore away from the distal bone fragment. Once a desired spacing of the distal and proximal bone fragments is achieved, through sufficient squeezing together of the first and second handle members, a screwdriver is used to engage the partially tightened bone screw. This screwdriver is rotated to gradually tighten the second bone screw, as the prongs of the second modified tip insert are gradually slid out from underneath the bone screw, finally resulting in a fully tightened second bone screw against the fixation plate, fixing the reduction as desired When it is desired to perform compression, rather than expansion, a replaceable tip insert having inwardly facing jaws and an inwardly facing plate engaging region is selected instead of replaceable tip insert 50. Alternatively, as discussed above, a bi-directional replaceable tip insert, having two substantially flat, planar regions disposed 180° opposite each other, is selected, and is attached to second handle member 30 such that its jaws face inwardly, towards bearing assembly 40. Moreover, as discussed above, an alternative embodiment of invention, having handle members cooperating in a scissors-like manner, may alternatively be employed for compression operations. Similar to the expansion procedure described above, once an inwardly facing tip is in place, fracture fixation expansion/compression instrument 10 is maneuvered into engagement with plate 80 and second bone screw 91, such that hexagonal tip 63 engages the recessed hexagonal head of partially tightened bone screw 91, and first jaw portion 55 is at least partially disposed through an aperture 82, such that plate engaging region 57 abuts an inwardly facing edge of aperture 82, as aperture 82 is releasably gripped between jaw portions 55 and 56. Screw 91 is placed in a more central region of the slotted hole for expansion and in a more peripheral region of the slotted hole for compression.

Next, the surgeon applies outward pressure or inward pressure (for the alternative, scissors-like configuration of the present invention) to elongated second ends 22 and 32 of first handle member 20 and second handle member 30, respectively, drawing them further apart or together (for the scissors-like configuration) from each other. This, in turn, causes hexagonal tip 63 and replaceable tip insert 50 to become less spaced apart from each other. As plate 80 has been securely affixed to the distal bone fragment using a first bone screw, this, in turn, cases a second bone screw to be drawn laterally towards the first bone screw, sliding along its associated slotted aperture 83. As the second bone screw has been partially threaded into the proximal bone fragment, this, in turn, causes the proximal bone fragment to be drawn displaced towards the distal bone fragment of the fracture. Once the two bone fragments have been drawn completely together, or once a desired spacing of the distal and proximal bone fragments is achieved, through sufficient movement of the elongated second ends of the first and second handle members, a handle attached to hexagonal driver 60 is rotated, to fully tighten the second bone screw against plate 80, fixing the reduction as desired.

In essence, both the "spreader" configuration of the present invention, in which pulling the gripping regions of the handle members together causes the opposing ends of the handle members to separate, and the "scissors" configuration of the present invention, in which pulling the gripping regions of the handle members together likewise cause the opposing ends of the handle members to be drawn together, can each be used in two separate respective expansion and compression applications, for a total of eight different expansion and compression applications, as summarized in the following paragraphs, with reference, in general, to the fixation plate 80 and first bone screw 90 secured to a distal fragment of a fracture, as shown in FIG. 7.

Spreader configuration expansion application 1: Gripping jaws 55 and 56 engage a hole 82 that is more central to plate 80 than the slotted hole 83 associated with second bone screw 91. Second bone screw 91 is placed in a central region of slotted hole 83. Bringing the gripping regions of the handle members together distracts screw 91 away from gripping jaws 55 and 56. Moreover, gripping jaws 55 and 56 are configured to engage a side of the central hole 82 that is opposite to the slotted hole 83 associated with second bone screw 91.

Spreader configuration compression application 1: Gripping jaws 55 and 56 engage a hole 82 that is more central to plate 80 than the slotted hole 83 associated with second bone screw 91. Second bone screw 91 is placed on through a peripheral side of it associated slotted hole 83. Separating the gripping regions of the handle members apart causes screw 91 to displace toward the central hole. Moreover, gripping jaws 55 and 56 are configured to engage a side of the central hole that is adjacent to the slotted hole 83 associated with second bone screw 91.

Spreader configuration expansion application 2: Gripping jaws 55 and 56 engage a hole 82b of plate 80 that is more peripheral to the slotted hole 83 associated with second bone screw 91, and screw 91 is disposed through a central portion of the slotted hole. Separating the gripping regions of the handle members apart causes second bone screw 91 to displace toward the more peripheral hole 82b. Moreover, gripping jaws 55 and 56 are configured to engage a side of peripheral hole 82b that is adjacent to the slotted hole 83 associated with second bone screw 91.

Spreader configuration compression application 2: Gripping jaws 55 and 56 engage a hole 82b of plate 80 that is more peripheral to the slotted hole 83 associated with second bone screw 91, and screw 91 is disposed through a peripheral side of the slotted hole. Bringing the gripping regions of the handle members together causes second bone screw 91 to displace away from the more peripheral hole 82b. Moreover, Gripping jaws 55 and 56 are configured to engage the side of peripheral hole 82b that is opposite to the slotted hole 83 associated with second bone screw 91.

Scissors configuration expansion application 1: Gripping jaws 55 and 56 engage a hole 82 that is more central to plate 80 than the slotted hole 83 associated with second bone screw 91. Second bone screw 91 is placed in a central region of slotted hole 83. Separating the gripping regions of the handle members apart distracts screw 91 away from gripping jaws 55 and 56. Moreover, gripping jaws 55 and 56 are configured to engage a side of the central hole 82 that is opposite to the slotted hole 83 associated with second bone screw 91.

Scissors configuration compression application 1: Gripping jaws 55 and 56 engage a hole 82 that is more central to plate 80 than the slotted hole 83 associated with second bone screw 91. Second bone screw 91 is placed on through a peripheral side of it associated slotted hole 83. Bringing the gripping regions of the handle members together causes screw 91 to displace toward the central hole. Moreover, gripping jaws 55 and 56 are configured to engage a side of the central hole that is adjacent to the slotted hole 83 associated with second bone screw 91.

Scissors configuration expansion application 2: Gripping jaws 55 and 56 engage a hole 82b of plate 80 that is more peripheral to the slotted hole 83 associated with second bone screw 91, and screw 91 is disposed through a central portion of the slotted hole. Bringing the gripping regions of the handle members together causes second bone screw 91 to displace toward the more peripheral hole 82b. Moreover, gripping jaws 55 and 56 are configured to engage a side of peripheral hole 82b that is adjacent to the slotted hole 83 associated with second bone screw 91.

Scissors configuration compression application 2: Gripping jaws 55 and 56 engage a hole 82b of plate 80 that is more peripheral to the slotted hole 83 associated with second bone screw 91, and screw 91 is disposed through a peripheral side of the slotted hole. Separating the gripping regions of the handle members apart causes second bone screw 91 to displace away from the more peripheral hole 82b. Moreover, Gripping jaws 55 and 56 are configured to engage the side of peripheral hole 82b that is opposite to the slotted hole 83 associated with second bone screw 91.

In all of the previously described embodiments, manual pulling together or separation of the actuators, or second ends of the handle members is employed to perform the expansion or compression of the fracture, respectively. However, alternative means of performing the expansion and compression are also contemplated. For example, one of the handle members may optionally include a male-threaded shaft rotatably attached to an interior surface of the handle. The shaft is disposed generally transverse to the handle member, and extends through a female threaded bore of the other handle member. A thumbwheel is disposed about the threaded shaft. Manipulation of the thumbwheel in a first direction, such as clockwise, causes the second ends of the handle members to be drawn towards each other. Manipulation of the thumbwheel in a second direction, such as counterclockwise, causes the second ends of the handle members to be drawn away from each other. Moreover, the male-threaded shaft and thumbwheel arrangement permits a desired spacing of the second ends of the handle members, and, in turn, a desired spacing of the hexagonal driver's head and plate engaging region of the replaceable tip insert, to be readily maintained.

Alternatively, one end of a shaft, or bar having a plurality of longitudinally aligned notches disposed thereon in a saw tooth-like manner may be attached to an interior surface of one handle member, with a cooperating protrusion, or "click stop" member, being attached to the other handle member. The notches and click stop member cooperate to permit the spacing of the gripping regions of the handle members, and, in turn, the spacing of the first ends of the handle members, to be releasably locked in a variety of predetermined positions.

It is to be understood that even though numerous characteristics and advantages of the present inventive surgical tool have been set forth herein, together with the details of the structure and function of several preferred embodiments of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A surgical tool for performing at least one of relative compression and expansion of a first bone fragment and a second bone fragment in cooperation with a fixation plate, the surgical tool comprising:
   a first handle member and a second handle member, the first and second handle members being pivotably attached to each other;
   a fixation plate engaging member coupled to the first handle member and configured to releasably engage at least a portion of the fixation plate;
   a fastener having an elongated body for affixation to a bone and a mating head portion configured for engagement by a fastener driver;
   a fastener driver having a first end engaging the mating head portion of the fastener and imparting rotational movement to the fastener upon rotation of the fastener driver while the fixation plate engaging member is engaged to the fixation plate;
   the second handle member having a driver accepting region having a cylindrical bore extending through at least a portion of the second handle member and permitting at least one of replaceable fastening and permanent fastening of at least a portion of the fastener driver to the surgical tool; and
   relative manipulation of the first and second handle members causing a spacing between the fixation plate engaging member and the first end of the fastener driver to be altered.

2. The surgical tool according to claim 1, wherein the fixation plate engaging member comprises a first jaw portion, a second jaw portion, and a plate engaging region disposed between the first and second jaw portions.

3. The surgical tool according to claim 1, wherein the fixation plate engaging member is releasably fastenable to the surgical tool.

4. The surgical tool according to claim 1, wherein the surgical tool further comprises a rotatable roller bearing assembly adapted to receive at least a portion of the fastener driver.

5. The surgical tool according to claim 4, wherein the bearing assembly is releasably fastenable to the surgical tool.

6. The surgical tool according to claim 1, wherein at least one of the handle members includes a gripping region.

7. The surgical tool according to claim 1, wherein the first handle member has a first gripping region, the second handle member has a second gripping region, the spacing between the fixation plate engaging member and the first end of the fastener driver increasing as a spacing between the first and second gripping regions is decreased, the spacing between the fixation plate engaging member and the first end of the fastener driver decreasing as the spacing between the first and second gripping regions is increased.

8. The surgical tool according to claim 1, wherein the fastener driver comprises a hexagonal driver.

9. The surgical tool according to claim 1, wherein the fastener driver is releasably fastenable to the surgical tool.

10. The surgical tool according to claim 1, wherein the fastener driver is permanently fastened to the surgical tool.

11. The surgical tool according to claim 1, wherein the fastener comprises a bone screw.

12. A surgical tool for performing at least one of relative compression and expansion of a first bone fragment and a second bone fragment in cooperation with a fixation plate, the surgical tool comprising:
   a fixation plate engaging member configured to releasably engage at least a portion of the fixation plate;
   a fastener having an elongated body for affixation to a bone and a mating head portion configured for engagement by a fastener driver;
   a fastener driver having a first end engaging a mating head portion of the fastener and imparting rotational movement to the fastener upon rotation of the fastener driver while the fixation plate engaging member is engaged to the fixation plate;
   a driver engaging member including a cylindrical bore for insertion of the fastener driver therethrough and permitting releasable engagement of at least a portion of a fastener driver by the surgical tool; and
   at least one actuator, manipulation of the actuator causing a spacing between the fixation plate engaging member and the driver engaging member to be altered, prompting collinear relative movement of the fixation plate engaging member and a fastener driver engaged.

13. The surgical tool according to claim 12, wherein the driver engaging member comprises a first prong member, a second prong member, and a slotted region disposed between the first and second prong members.

14. A surgical tool for performing at least one of relative compression and expansion of a first bone fragment and a second bone fragment in cooperation with a fixation plate, the surgical tool comprising:
   a fixation plate engaging member configured to releasably engage at least a portion of the fixation plate;
   a fastener having an elongated body for affixation to a bone and a mating head portion configured for engagement by a fastener driver;
   a fastener driver disposed through a cylindrical bore of the surgical tool configured to releasably engage at least a portion of the fastener and having a first end engaging a mating head portion of the fastener and imparting rotational movement to the fastener upon rotation of the fastener driver while the fixation plate engaging member is engaged to the fixation plate; and
   at least one actuator, manipulation of the actuator causing a spacing between the fixation plate engaging member and the fastener engaging member to be altered, prompting collinear relative movement of the fixation plate engaging member and the fastener driver.

15. The surgical tool according to claim 14, wherein the at least one actuator comprises at least two actuators having longitudinal axes, and wherein the driver is fastenable to the surgical tool with a longitudinal axis of the fastener driver and the longitudinal axes of the at least two actuators all being collinear to each other.

16. The surgical tool according to claim 1, wherein manipulation of the actuator prompts substantially collinear relative movement of the fixation plate engaging member and the first end of the fastener driver.

17. The surgical tool according to claim 1, wherein the driver accepting region permits at least a portion of the fastener driver to be carried internally within at least a portion of the surgical tool.

18. The surgical tool according to claim 1, wherein, upon fastening of the at least a portion of the fastener driver to the surgical tool, angular movement of the fastener driver relative to the surgical tool is substantially precluded.

19. The surgical tool according to claim 1, wherein the surgical tool further comprises a bearing assembly having a rotatable roller bearing and adapted to receive at least a portion of the fastener driver.

20. The surgical tool according to claim 1, wherein the surgical tool is capable of performing both relative compression and expansion of the first bone fragment and the second bone fragment in cooperation with the fixation plate, the at least one fastener, and the fastener driver.

21. The surgical tool according to claim 1, wherein the at least one actuator comprises at least two actuators having longitudinal axes, and wherein the fastener driver is fastenable to the surgical tool with a longitudinal axis of the fastener driver and the longitudinal axes of the at least two actuators all being collinear to each other.

22. The surgical tool according to claim 1, wherein the surgical tool further includes a locking member serving to lock at least a portion of the fastener driver in position proximate the fastener accepting region.

* * * * *